United States Patent
Maurer et al.

(10) Patent No.: US 10,729,622 B2
(45) Date of Patent: Aug. 4, 2020

(54) PROCESS FOR TAKING A DENTAL IMPRESSION AND CURABLE COMPOSITION FOR USE IN A DENTAL IMPRESSIONING AND RETRACTION PROCESS

(71) Applicant: 3M INNOVATIVE PROPERTIES COMPANY, St. Paul, MN (US)

(72) Inventors: Andreas R. Maurer, Langenneufnach (DE); Joachim W. Zech, Kaufering (DE); Christoph Schulte, Windach (DE); Peter U. Osswald, Tuerkheim (DE); Rudolf Schmid, Eichenau (DE); Hendrik Grupp, Ammersee (DE); Marc Peuker, Schoendorf (DE); Helmut Pauser, Diessen (DE); Manfred Harre, Landsberg am Lech (DE); Andreas J. Boehm, Reichling (DE)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 0 days.

(21) Appl. No.: 15/574,766

(22) PCT Filed: May 19, 2016

(86) PCT No.: PCT/US2016/033303
§ 371 (c)(1),
(2) Date: Nov. 16, 2017

(87) PCT Pub. No.: WO2016/196028
PCT Pub. Date: Dec. 8, 2016

(65) Prior Publication Data
US 2018/0221248 A1  Aug. 9, 2018

(30) Foreign Application Priority Data

May 29, 2015 (EP) .................................... 15169801

(51) Int. Cl.
*A61K 6/18* (2020.01)
*A61K 6/71* (2020.01)
(Continued)

(52) U.S. Cl.
CPC ............... *A61K 6/18* (2020.01); *A61C 9/00* (2013.01); *A61C 9/0006* (2013.01);
(Continued)

(58) Field of Classification Search
CPC ...... A61K 6/0011; A61K 6/0073; A61K 6/10; A61K 6/18; A61K 6/71; A61K 6/90;
(Continued)

(56) References Cited

U.S. PATENT DOCUMENTS

| 4,167,618 A | 9/1979 | Schmitt |
| 4,468,202 A | 8/1984 | Cohen |

(Continued)

FOREIGN PATENT DOCUMENTS

| EP | 0231420 | 8/1987 |
| EP | 0269071 | 6/1988 |

(Continued)

OTHER PUBLICATIONS

Kugel, "Investigation of a New Approach to Measuring Contact Angles for Hydrophilic Impression", Mar.-Apr. 2007, vol. 16, No. 2, pp. 84-92.

(Continued)

*Primary Examiner* — Cris L. Rodriguez
*Assistant Examiner* — Hao D Mai
(74) *Attorney, Agent, or Firm* — 3M Innovative Properties Company

(57) ABSTRACT

A process for taking a dental impression and/or conducting a dental retraction. The process includes the steps of:
(a) providing a composition (A) having the consistency (a1), composition (A) including curable components,
(Continued)

and a catalyst suitable to initiate or catalyze the curing of the curable components, composition (A) being contained in a device,
(b) applying a portion (I) of composition (A) with a consistency (a2) into the sulcus of a tooth,
(c) applying a portion (II) of composition (A) with a consistency (a1) in contact with composition (A) applied in step (b),
(d) removing portion (I) together with portion (II) of composition (A) from the surface of the tooth, consistency (a2) being higher than consistency (a1).

12 Claims, 3 Drawing Sheets

(51) Int. Cl.
A61K 6/90 (2020.01)
A61C 9/00 (2006.01)
(52) U.S. Cl.
CPC .......... *A61C 9/0026* (2013.01); *A61C 9/0033* (2013.01); *A61K 6/71* (2020.01); *A61K 6/90* (2020.01)
(58) Field of Classification Search
CPC ....... A61C 9/00; A61C 9/0006; A61C 9/0026; A61C 9/0033
See application file for complete search history.

(56) References Cited

U.S. PATENT DOCUMENTS

| | | | |
|---|---|---|---|
| 4,657,959 A | 4/1987 | Bryan | |
| 4,782,101 A | 11/1988 | Waller | |
| 5,145,886 A | 9/1992 | Oxman | |
| 5,830,951 A * | 11/1998 | Fiedler | A61K 6/90 525/478 |
| 6,048,202 A * | 4/2000 | Jensen | A61C 5/82 433/136 |
| 6,376,569 B1 | 4/2002 | Oxman | |
| 7,549,862 B2 * | 6/2009 | Kollefrath | A61C 9/0033 433/136 |
| 8,470,905 B2 * | 6/2013 | Dragan | A61C 9/0033 106/35 |
| 8,998,610 B2 * | 4/2015 | Pauser | A61C 5/62 433/90 |
| 9,044,288 B2 * | 6/2015 | Angeletakis | A61C 9/0033 |
| 2005/0069838 A1 * | 3/2005 | Kollefrath | A61K 6/90 433/136 |
| 2005/0118552 A1 * | 6/2005 | Coopersmith | A61C 9/0033 433/136 |
| 2006/0286510 A1 * | 12/2006 | Boghosian | A61C 9/00 433/214 |
| 2008/0271636 A1 * | 11/2008 | Kim | A61K 6/90 106/35 |
| 2009/0061393 A1 * | 3/2009 | Kollefrath | A61C 9/0033 433/226 |
| 2009/0274999 A1 * | 11/2009 | Coopersmith | A61C 8/0001 433/218 |
| 2010/0183999 A1 * | 7/2010 | Klettke | A61K 6/78 433/89 |
| 2010/0261143 A1 * | 10/2010 | Hampe | A61K 6/18 433/215 |
| 2011/0046262 A1 | 2/2011 | Bublewitz | |
| 2012/0045732 A1 | 2/2012 | Chen | |
| 2012/0329006 A1 * | 12/2012 | Pierson | A61C 9/0026 433/90 |
| 2013/0030076 A1 * | 1/2013 | Weinmann | C08K 5/0025 522/31 |
| 2013/0183630 A1 * | 7/2013 | Krikorian | C08L 71/02 433/3 |
| 2014/0050043 A1 | 2/2014 | Durali | |
| 2014/0170596 A1 | 6/2014 | Angeletakis | |
| 2015/0024341 A1 | 1/2015 | Pauser | |
| 2018/0132979 A1 * | 5/2018 | Richter | A61C 9/0026 |
| 2018/0177574 A1 * | 6/2018 | Dubey | A61K 6/90 |
| 2019/0110960 A1 * | 4/2019 | Maurer | A61K 6/18 |

FOREIGN PATENT DOCUMENTS

| | | |
|---|---|---|
| EP | 0398701 | 11/1990 |
| EP | 0480238 | 4/1992 |
| EP | 2380925 | 10/2011 |
| EP | 2698124 | 2/2014 |
| WO | WO 2007-016295 | 2/2007 |
| WO | WO 2009-151983 | 12/2009 |
| WO | WO 2011-133495 | 10/2011 |
| WO | WO 2012-177985 | 12/2012 |
| WO | WO 2014-050043 | 4/2014 |
| WO | WO 2016-196027 | 12/2016 |
| WO | WO 2016-196048 | 12/2016 |
| WO | WO 2017-007676 | 1/2017 |

OTHER PUBLICATIONS

International Search Report for PCT International Application No. PCT/US2016/033303, dated Aug. 17, 2016, 5pgs.

* cited by examiner

PROCESS FOR TAKING A DENTAL IMPRESSION AND CURABLE COMPOSITION FOR USE IN A DENTAL IMPRESSIONING AND RETRACTION PROCESS

FIELD OF THE INVENTION

The invention relates to a process for taking a dental impression by using a curable composition in two different viscosity states. The invention also relates to such a curable composition for use in such a process.

BACKGROUND ART

Producing dental replacement parts like crowns and bridges requires the exact determination of the dental situation in the mouth of the patient. Otherwise, the dental replacement parts will not accurately fit.

For determining the dental situation in the mouth of a patient different methods are know. Besides imaging and computer based methods, a huge portion of this task is still accomplished by using conventional dental impression materials.

Dental impression materials can be classified according to their curing mechanism (e.g. addition curing or condensation curing). Dental impression materials can also be classified according to their consistency. Besides low viscous dental impression materials, there exists highly viscous, so-called putty like dental impression materials.

Dental impression materials are typically provided as two component systems which consist of a base and a catalyst paste and which are mixed before use.

Due to its high viscosity, mixing putty like dental impression materials with an automated system like the Pentamix™ device (3M ESPE) can be difficult. Thus, often putty like dental impression materials are mixed (i.e. kneaded) by hand.

The materials are typically pasty and cure in the mouth of the patient due to a chemical curing mechanism. The cured material is removed from the mouth of the patient and the obtained impression represents a negative image of the dental situation. The impression is then typically filled with plaster to obtain a positive model. The positive model is used for designing the desired dental replacement part.

However, for capturing the surface details of the subgingival regions of the hard dental tissue, i.e. the region below the gum line, conducting a dental retraction process is typically needed. Capturing those surface details is important if a dental replacement part is desired, which fits well to the surface of the prepared tooth. Currently, different kinds of retraction processes and materials are known.

Many dentists still use dental retraction cords, which are placed in the sulcus of the tooth, remain there for a sufficient period of time and are removed later before conducting the impression process.

Alternatively, a dental retraction material can be used, which is inserted into the sulcus, kept there for a sufficient period of time and which is removed, as well, before the impression process is conducted.

In order to function as dental retraction material, the material has to have a certain stiffness or viscosity, which allows the retraction material to keep the sulcus open (withstand sulcus pressure).

A commercially available dental retraction material is e.g. provided by 3M ESPE under the brand 3M™ ESPE™ Retraction Capsule or 3M™ ESPE™ Astringent Retraction Paste, respectively.

In contrast to dental retraction materials, a dental impression material has to show good flowing properties and has typically a thin consistency. Conducting such a separate retraction step is time consuming. Patients and dentists nowadays have an increasing demand for a simplified method for taking dental impressions.

WO 2012/177985 A2 (Dentsply) relates to a tissue management impression material and a method of application into the sulcus of a patient, whereby the tissue management impression material is a part of the final dental impression made when manufacturing a dental device, such as a crown.

US 2012/0045732 A1 (Chen et al.) describes a dental paste dispensing device having a modified dispensing end for atraumatic contact with soft tissue.

US 2011/0046262 A1 (Bublewitz et al.) describes pasty masses that are suitable as insert material for widening the gingival sulcus. The materials described contain a paste-forming agent, superabsorber particles and at least one astringent.

US 2014/050043 A1 (Durali et al.) relates to a universal dental impression material system using a programmable device having containers for separately housing two or more components that form a dental impression material when mixed.

US 2014/0170596 A1 (Angeletakis) describes a two part retraction system than can be inserted into the sulcus to form a semi-rigid porous elastomer releasing a hemostatic agent suitable for sulcus retraction such that a dental impression may be completed by a dental practitioner.

U.S. Pat. No. 4,468,202 (Cohen) describes a method of obtaining a dental impression comprising the steps of retracting gingival tissue by applying a photocurable or chemical curable elastomeric material into the space between the teeth and the gingival tissue, curing the elastomeric material to a certain degree, applying a second photocurable or chemically curable elastomeric material in contact with the subgingivally applied elastomeric material, curing the elastomeric material to a certain degree and removing the cured elastomeric composite. It is described that the two elastomeric materials are contained in containers separated from each other, from which the material may be selectively expelled.

DESCRIPTION OF THE INVENTION

There is a need for a simplified process for taking dental impressions and a material or device which can be used in such a process.

In particular it would be desirable, if the process of retraction and impressioning can be somehow combined, ideally using only one material.

Ideally the material used for conducting the retraction step is incorporated and becomes part of the material used for conducting the impression step. The invention describes in the present text addresses one or the other needs described above.

In one embodiment the present invention features a process for taking a dental impression and/or conducting a dental retraction of dental tissue as described in the present text, the process comprising the steps of:
  (a) providing a composition (A) having the consistency (a1), composition (A) comprising curable components, and a catalyst suitable to initiate or catalyze the curing of the curable components, composition (A) being contained in a device, (b) applying a portion (I) of composition (A) with a consistency (a2) into the sulcus of a tooth, (c) applying a portion (II) of composition (A) with a consistency (a1) in contact with composition (A) applied in step (b), (d) removing portion (I) together with portion (II) of composition (A) from the surface of the tooth, consistency (a2) being higher than consistency (a1).

More particularly, the invention relates to a process for taking a dental impression and/or conducting a dental retraction of dental tissue as described in the present text, the process comprising the steps of:

(a) providing a composition (A) having the consistency (a1), composition (A) being contained in a device, in particular a packaging device, composition (A) comprising curable components, and a catalyst suitable to initiate or catalyze the curing of the curable components, (b) modifying the consistency of a portion (I) of composition (A) to a consistency (a2), (c) applying the portion (I) of composition (A) having consistency (a2) into the sulcus of a tooth, (d) applying a portion (II) of composition (A) having consistency (a1) in contact with composition (A) applied in step (c), preferably so that the visible surface of the tooth is covered, (e) removing portion (I) together with portion (II) of composition (A) from the surface of the tooth, consistency (a2) being higher or larger than consistency (a1).

The invention is also related to a kit of parts comprising the composition described in the present text and an instruction of use describing the process steps of the process described in the present text.

In another embodiment, the invention relates to a composition for use or to be used in a process as described in the text of the invention.

Definitions

Unless defined differently, for this description the following terms shall have the given meaning:

A "dental composition" or a "composition for dental use" or a "composition to be used in the dental field" is any composition which can be used in the dental field. In this respect the composition should not be detrimental to the patients' health and thus free of hazardous and toxic components being able to migrate out of the composition. Examples of dental compositions include permanent and temporary crown and bridge materials, artificial crowns, anterior or posterior filling materials, adhesives, mill blanks, lab materials and orthodontic devices. Dental compositions are typically hardenable compositions, which can be hardened at ambient conditions, including a temperature range from about 15 to 50° C. or from about 20 to 40° C. within a time frame of about 30 min or 20 min or 10 min. Higher temperatures are not recommended as they might cause pain to the patient and may be detrimental to the patient's health. Dental compositions are typically provided to the practitioner in comparable small volumes, that is volumes in the range from about 0.1 to about 500 ml or from about 0.5 to about 100 ml or from about 1 to about 50 ml. Thus, the storage volume of useful packaging devices is within these ranges.

A "dental impression material" is a material used for making impressions of the tooth structure including the gingiva. A dental impression material is usually applied on a dental impression tray. A dental impression material can be based on different chemical substances and crosslink by various chemical reactions (including addition curing and condensation curing materials). Typical examples include silicone based impression materials (e.g. VPS materials) and polyether based impression materials and mixtures of those.

A "putty like dental impression material" is a kneadable dental impression material having a consistency of 35 mm or below according to ISO 4823.

A "dental retraction material" is a material intended to be placed in the gingival sulcus, that is, the natural space between the hard dental tissue (i.e. tooth structure) and the gum tissue that surrounds the hard dental tissue. Once placed in the gingival sulcus, the dental retraction material will exert pressure on the surrounding tissue resulting in a widening of the gingival sulcus to enable the practitioner to get a more precise impression of the dental situation below the gum line during a dental impression process. Like a dental impression material, a dental retraction material is removed from the mouth of the patient after use.

"Consistency" describes the flowing behaviour of a composition or material under load, in particular, if the composition or material is located in a mould. A composition or material having a high consistency shows a reduced flowing behaviour under load compared to a composition or material having a low consistency. A hardened composition or material has a very high consistency as this composition or material does essentially not show any flowing behaviour under load.

"Dental tissue" means the hard and soft dental tissue. Hard dental tissue comprises the tissue of dental tooth (including dentin and enamel). Soft dental tissue comprises the tissue surrounding the hard dental tissue, i.e. the gum.

The term "compound" or "component" is a chemical substance which has a particular molecular identity or is made of a mixture of such substances, e.g., polymeric substances.

A "liquid" is any solvent or liquid which is able to at least partially disperse, dissolve or suspend the components being present in the inventive composition at ambient conditions (e.g. 23° C.).

By "paste" is meant a soft, viscous mass of solids (i.e. particles) dispersed in a liquid.

A "particle" or "particulate filler" means a substance being a solid having a shape which can be geometrically determined. The shape can be regular or irregular. Particles can typically be analysed with respect to e.g. grain size and grain size distribution. A particulate filler is composed of free-flowing particles.

"Room temperature hardening or curing" implies that the curing reaction can proceed at temperatures at or near 25° C. For example, the oral cavity of the mouth has an average temperature of approximately 32° C. and is therefore near room temperature. Certain "high" temperature cured materials are designed to cure only at relatively high temperatures (e.g., >50° C. or >100° C.) and are stable (i.e., the curing reaction is inhibited) at room temperature.

The term "silicone," as used herein, refers to a polymer having, for the most part, alternating silicon and oxygen atoms (i.e., a polysiloxane chemical structure) and having sufficient pendant functional groups to undergo a setting reaction in the presence of a crosslinker compound and a catalyst compound.

"Poly" means that the respective substance contains at least 10 repeating units of a certain monomer moiety.

The term "hydrosilation" means the addition of a compound comprising SiH-groups to a compound containing an aliphatic multiple bond (e.g., an olefinic or acetylenic unsaturation), preferably a vinyl group, —CH=CH$_2$.

The terms "vulcanizing, hardening, crosslinking, setting, curing" are used interchangeable and refer to silicones that have as a common attribute the development of a cross-linked elastomer from relatively low molecular weight linear or branched polymers by means of a chemical reaction that simultaneously forms these crosslinks and effectively extends chain length at room temperature.

"Hydrophilating agents" are agents that are able to either lower the surface tension of water, if used alone (like surfactants), or contribute to a lower surface tension, if used in combination with a surfactant (sometimes referred to as wetting-enabler). If desired, the effect of lowering the surface tension of water can be measured by determining the water-contact angle as described in more detail below.

"Ambient conditions" mean the conditions which the inventive solution is usually subjected to during storage and handling. Ambient conditions may, for example, be a pressure of 900 to 1100 mbar, a temperature of 10 to 40° C. and a relative humidity of 10 to 100%. In the laboratory ambient conditions are adjusted to 20 to 25° C. and 1000 to 1025 mbar.

A composition is "essentially or substantially free of" a certain component, if the composition does not contain said component as an essential feature. Thus, said component is not willfully added to the composition either as such or in combination with other components or ingredient of other components. A composition being essentially free of a certain component usually does not contain that component at all. However, sometimes the presence of a small amount of the said component is not avoidable e.g. due to impurities contained in the raw materials used.

As used herein, "a", "an", "the", "at least one" and "one or more" are used interchangeably. The terms "comprises" or "contains" and variations thereof do not have a limiting meaning where these terms appear in the description and claims. Also herein, the recitations of numerical ranges by endpoints include all numbers subsumed within that range (e.g., 1 to 5 includes 1, 1.5, 2, 2.75, 3, 3.80, 4, 5, etc.).

Adding an "(s)" to a term means that the term should include the singular and plural form. E.g. the term "additive(s)" means one additive and more additives (e.g. 2, 3, 4, etc.).

Unless otherwise indicated, all numbers expressing quantities of ingredients, measurement of physical properties such as described below and so forth used in the specification and claims are to be understood as being modified in all instances by the term "about". The term "comprise" shall include also the terms "consist essentially of" and "consists of".

DETAILED DESCRIPTION OF THE INVENTION

Figure 1:
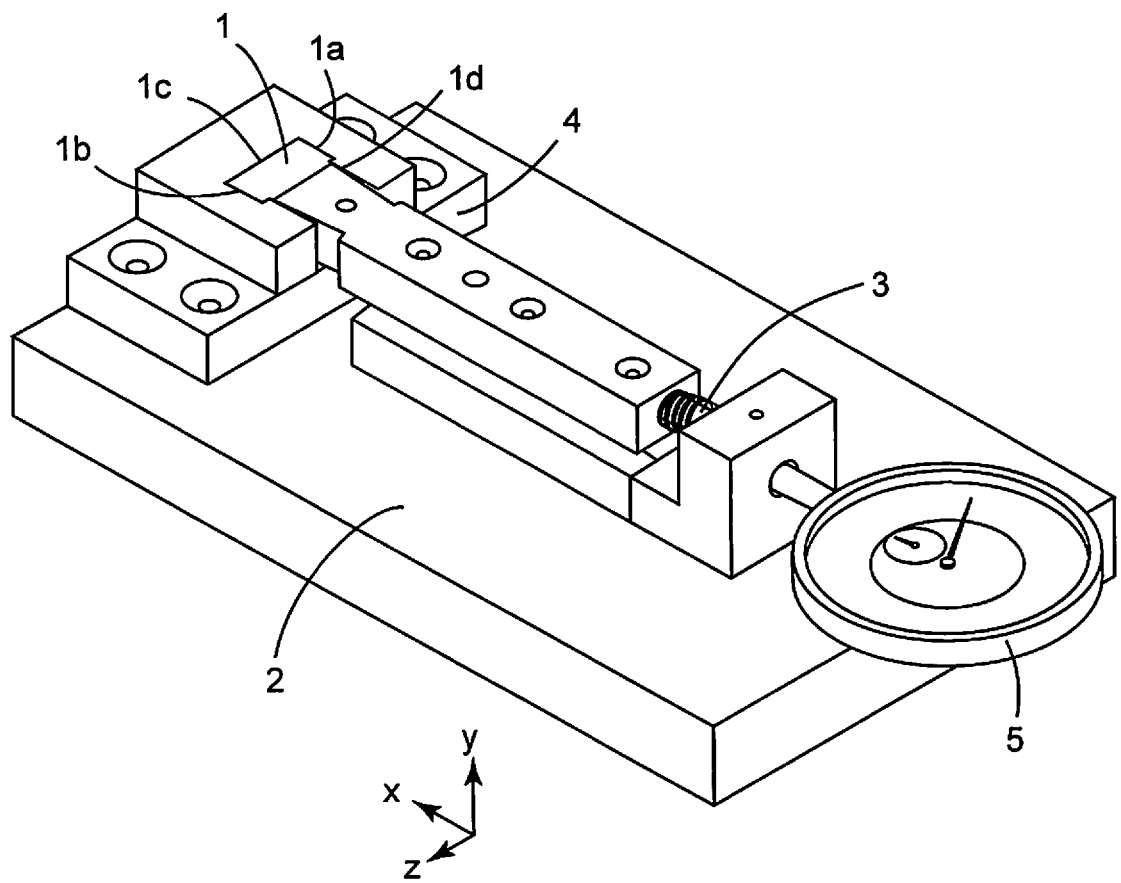
FIG. 1 shows a device which can be used for determining the consistency of the curable composition.

The invention is advantageous in a variety of aspects.

It has been found that the process and composition described in the present text allows the combination of dental impression and dental retraction in one system or device, so that the dentist does not have to use two different kind of materials, i.e. a dental retraction material and a dental impression material to obtain a high accurate negative image of the dental situation in the mouth of a patient.

This can be done by changing the consistency of the curable composition during the process.

That is, the curable composition is able to act as dental retraction material on the one side and as dental impression material on the other side, depending on its consistency, which can be adjusted.

The change in consistency of the composition is undertaken or performed before the composition is applied to the dental tissue.

Thus, the invention describes a process allowing the practitioner to perform a dental retraction process and dental impression process using ideally only one kind of material, the consistency of which can be adjusted.

In a first step the material is used for performing the retraction step. In a further step, the material is used for performing the impression step.

The process described in the present text is focussed on taking a dental impression by combining both steps.

The dental impression is intended to cover or record the surface details of one or more teeth as a negative image using a curable composition.

With the dental impression process described in the present text not only the surface of the tooth or teeth above the gum line (i.e. supragingival) should be covered, but, if possible, also the surface of the tooth or teeth below the gum line (i.e. subgingival).

In order to cover subgingival regions as well, the composition used for taking the impression should also be able to be inserted into the sulcus of the respective tooth or teeth. The composition should also be able to remain in the sulcus at least for a time sufficient to effect a retraction, that is, widening of the sulcus to make the subgingival regions of the tooth or teeth accessible for the impression material.

The composition (A) described in the present text is typically contained in a device, in particular a device suitable for storing and packaging. Suitable devices include cartridges, barrels, foil bags and syringes. The device can comprise a nozzle or is adapted to receive a nozzle.

The nozzle has typically a shape which allows the nozzle to be inserted into the sulcus of a tooth. The nozzle is typically conically shaped. The nozzle may be located at the front end of a static mixing tip.

The device may also comprises a plunger or a pump. By moving the plunger in the direction of the nozzle or switching the pump on, the composition contained in the device can be dispensed. According to one embodiment, composition (A) is contained in a device comprising a nozzle.

A suitable device comprising a nozzle for applying composition (A) into the sulcus of a patient is described in WO 2009/151983 (3M). The content of this reference is herewith in corporate by reference.

According to one embodiment the device is characterized by at least one or more or all of the following features:
a) comprising at least two compartments (I) and (II);
b) volume of compartments (I) and (II): 1 ml to 50 ml or from 1 to 25 ml.

A typical dispensing speed for composition (A) being contained in the device is from 1 ml/s to 100 ml/s.

If the composition (A) to be used in the process described in the present text is prepared by mixing a base paste and a catalyst paste, the device typically contains at least two compartments or barrels, each of which contains a separate plunger.

According to one embodiment, the plungers can be moved independently from each other.

According to a further embodiment, the device comprises three compartments or barrels, each of which contains a separate plunger.

The first compartment contains the curable components. The second compartment contains the catalyst. The third compartment contains a modifying agent. On demand, the modifying agent can be added to the mixture of the curable components and the catalyst.

A device suitable for dispensing composition (A) is described in US 2014/0050043 A1 (Durali et al.). The content of this reference is herewith in corporate by reference. Upon providing the composition (A), the composition (A) has a consistency (a1).

Before applying a portion of the composition (A) through a nozzle into the sulcus of a tooth, the consistency of composition (A) contained in the device is modified to obtain a composition (A) having a consistency (a2).

The consistency (a2) is higher than the consistency (a1) of composition (A). Thus, that portion of composition (A) contained in the device and intended to be inserted into the sulcus of a tooth has a higher consistency than the consistency of composition (A) contained in the device before conducting the modification step.

In one embodiment, composition (A) is already hardened when inserted into the sulcus of a tooth. A hardened composition can be classified as having a consistency (a3).

The consistency (a3) of a hardened composition (A) is typically higher than consistency (a2) of a non-hardened composition (A).

According to one embodiment consistency (a2) is essentially the same as consistency (a3).

Once inserted, portion (I) of composition (A) having consistency (a2) contributes to the retraction of the sulcus, i.e. exerting pressure on the surrounding gingival and thus contributing to widening the sulcus and thus making the subgingival regions of the tooth accessible for the impression material.

The portion (I) of composition (A) having consistency (a2) remains in the sulcus for a time sufficient to effect the desired retraction. A typical time frame is from 0.01 to 10 or from 0.01 to 8 min.

During that time frame, the consistency (a2) of composition (A) may further change. In particular, the consistency of composition (A) contained in the sulcus typically increases and composition (A) may even harden to reach a consistency (a3).

The values of consistency (a1) and consistency (a2) determined at 23° C. may differ from each other by a factor of at least 2, 5, 10 or 20, if determined according to the method described in the Example section.

In a further step, a portion (II) of composition (A) contained in the device is applied without modification of the consistency and brought in contact with composition (A) which is present in the sulcus of the tooth.

Portion (II) of composition (A) having consistency (a1) is applied on top of portion (I) of composition (A) which has been applied with consistency (a2) before.

As from a chemical point of view the same material is used and applied, portion (I) and portion (II) of composition (A) will adhere or stick together.

The volume of portion (I) of composition (A) is typically lower than the volume of portion (II) of composition (A), typically at least by a factor of 2 or 5 or 10 or 15.

The volume of portion (II) of composition (A) is typically such that the visible surface of the tooth to be imaged is covered.

According to one embodiment, the process can be further characterized by at least one or more of the following features:

Volume of portion (I) of composition (A), if applied to the dental tissue of one tooth: from 5 $mm^3$ to 500 $mm^3$ or from 10 $mm^3$ to 400 $mm^3$ or from 15 to 300 $mm^3$ measured at 23° C.;

Volume of portion (II) of composition (A), if applied to the dental tissue of one tooth: from 0.5 to 15 ml or from 1 to 13 ml or from 1.5 to 10 ml measured at 23° C.

If desired, the consistency can be determined as follows:
providing a mould having a rectangular shape with the dimensions x (depth)=7.5 mm, y (width)=18 mm and z (height)=12 mm, the mould being formed by three immovable and one movable sidewall, all located on a plane surface, the movable sidewall being equipped with a spring having a defined spring pressure of 20 N, x being the distance between the movable sidewall and the opposing immobile sidewall,
compressing and fixing the spring,
filling composition (A) into the mould,
removing the fixation of the spring 60 s after having modified the consistency,
measuring the value x 70 s after having modified the consistency.

In a next step, portion (I) and portion (II) of composition (A) are removed from the surface of the tooth or teeth to be captured or imaged.

If a curable composition was used as composition (A), the removal is typically done once composition (A) is hardened.

According to a further embodiment, removal of portion (I) and portion (II) of composition (A) is done by applying a curable composition (B) on top of composition (A).

Composition (B) is typically contained in a dental tray.

The consistency of composition (B) is typically higher than the consistency (a1) of composition (A), but lower than the consistency (a2) of composition (A).

According to this embodiment, composition (A) having consistency (a2) can be regarded as "dental retraction material". Composition (A) having consistency (a1) can be regarded as so-called "dental wash-material". Composition (B) can be regarded as so-called "dental tray-material".

During use, the dental retraction material combines with the dental wash material and finally forms a part of the dental tray material.

The dental tray material is used as a kind of means or carrier for facilitating the removal of the dental retraction and dental wash material.

In FIGS. 2a to 2e the process described in the present text is further illustrated.

Figure 2A:
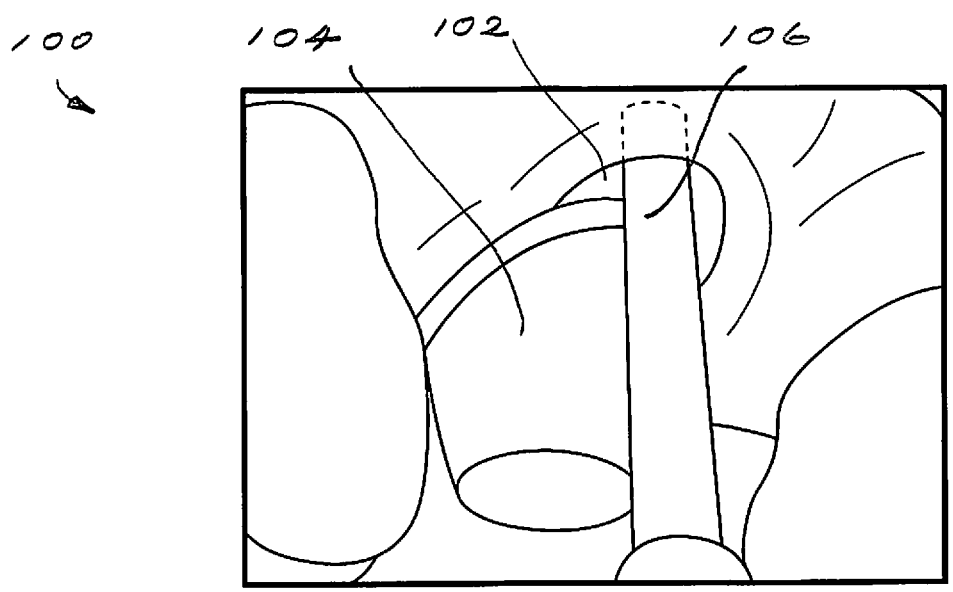
FIGS. 2a-2e illustrates certain steps of the process described in the present invention.

In step 100 of FIG. 2a, the sulcus 102 of a prepared tooth 104 is shown. Into the sulcus 102 a nozzle 106 attached to a packaging device (not shown) is inserted.

Figure 2B:
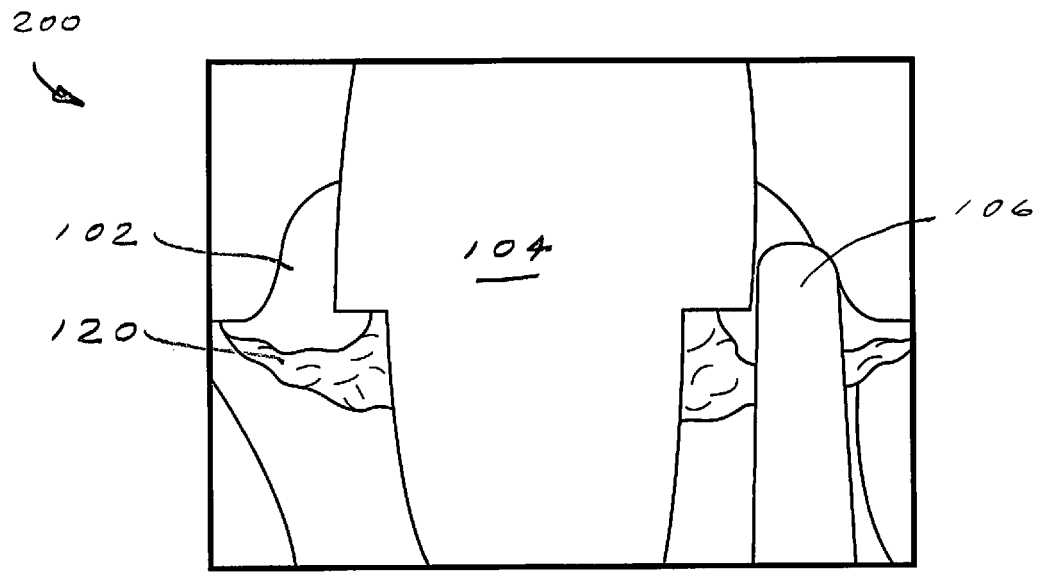

In step 200 of FIG. 2b, the application of a portion (I) of composition (A) 120 having consistency (a2) into the sulcus 102 through the nozzle 106 is shown. This step represents the so-called "dental retraction mode".

Figure 2C:
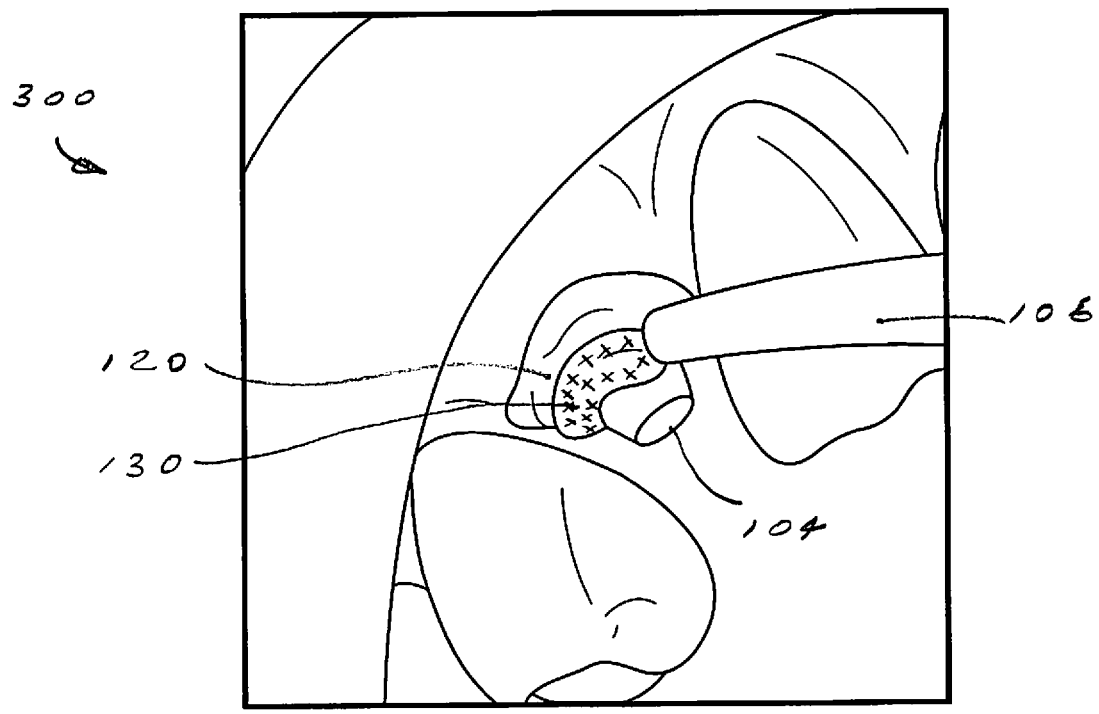

In step 300 shown in FIG. 2c, the application of a portion (II) of composition (A) 130 having consistency (a1) on top of the previously applied composition 120 of FIG. 2b is shown in cross section. This step represents the so-called "dental impression mode". For better visibility portion (II) of composition (A) is coloured or shaded differently.

Figure 2D:
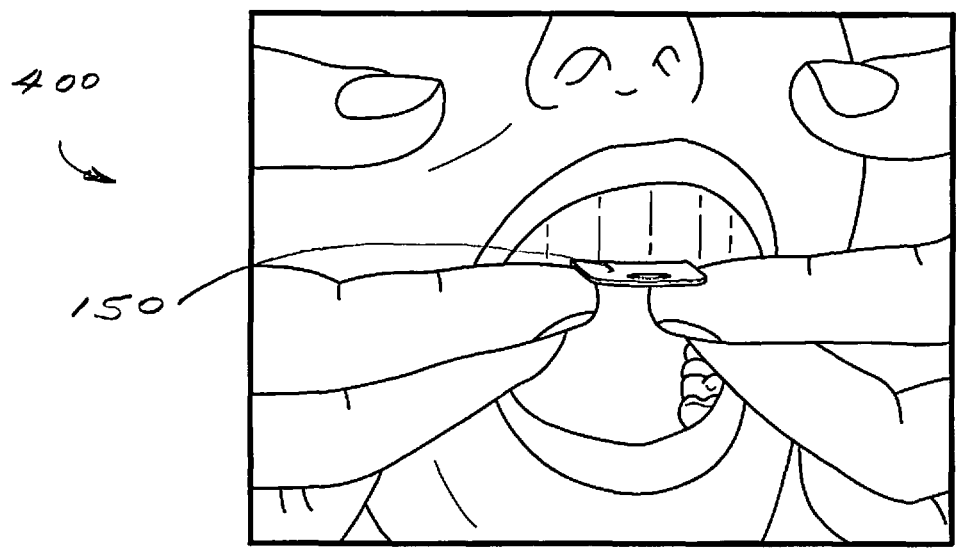

In step 400 of FIG. 2d, the application of a dental tray 150 containing composition (B)—not shown—is shown.

Figure 2E:
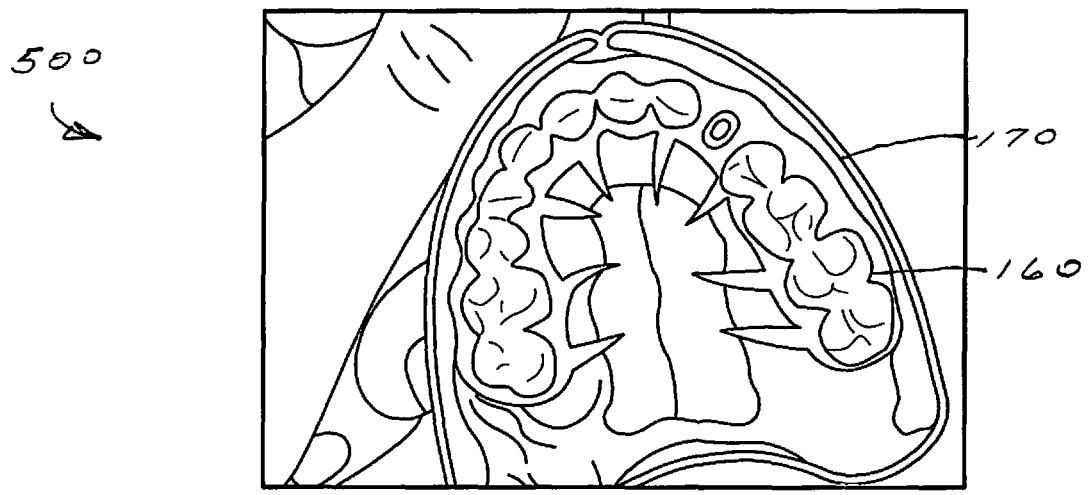

In step 500 shown in FIG. 2e, a dental impression 160 is shown, being contained in a dental tray 170. The dental impression contains composition (A) 140 which was inserted into the sulcus of a prepared tooth and composition (B) 142. Composition (A) 140 now forms an integral part of the whole dental impression 160. For the sake of better visibility, composition (A) 140 having been applied with consistency (a2) 130, composition (A) having been applied with consistency (a1) 120 and composition (B) 142 are coloured or shaded differently.

In the process described in the present text, composition (A) is used and applied in at least two different consistencies. Initially, composition (A) contained in the device has a consistency (a1).

After having conducted a modification step, composition (A) dispensed from the device and to be inserted into the sulcus of a tooth has a consistency (a2).

It can be preferred, if the increase in consistency from consistency (a1) to consistency (a2) or decrease from consistency (a2) to consistency (a1) is sufficient steep and fast enough to enable the practitioner to easily switch from one mode (retraction mode) to another mode (impression mode) and vice versa.

The modification of the consistency can be achieved by different means.

According to one embodiment, the modification of the consistency is achieved by physical means.

According to another embodiment, the modification of the consistency is achieved by chemical means.

Yet, according to a further embodiment, the modification of the consistency is achieved by a combination of physical means and chemical means.

Physical means to modify the consistency of composition (A) include heat, radiation and ultrasound.

Application of heat includes the increase of the temperature of composition (A) before composition (A) is applied into the sulcus of a tooth.

Applying heat to a curable composition typically leads to an increase of the curing speed of curable composition (A). This typically results in an increased consistency within a shorter period of time.

Heat can be applied by any means known to the technical practitioner.

E.g. heat can be generated by mixing the composition, e.g. the usage of very small mixing tips or nozzles where the composition to be mixed is passed through or by using an external heat source, like heat coils or other heating elements. The heat source can be located before or after a mixing zone for composition (A).

In order to avoid any damage or irritation of the soft and hard dental tissue, the temperature of composition (A) having consistency (a2) should not be above 40° C. Typically the temperature is in a range from 30 to 40° C.

Application of radiation includes the treating of composition (A) with light having a wavelength from 250 to $2 \times 10^6$ nm or from 300 to $1 \times 10^6$ nm. Thus, radiation can be applied in the form of infrared light, visible light and microwaves.

Radiation can be applied by means known to the technical practitioner. Typical means include typical light sources like LEDs or microwave generators.

The radiation source can be incorporated into the device. For guiding the light or radiation to the desired location, optical fibre(s) or light guiding layers, which may be made out of a plastic material, can be used. If desired, such a layer can be coated with metal for increasing the reflection properties.

The optical fibre(s) or layer(s) can be placed on top or around the device, but also in a zone along the nozzle or even within the device.

The application of radiation for modifying the consistency of composition (A) is in particular effective, if the curable component(s) of composition (A) are radiation-sensitive. In this respect, the catalyst should ideally be radiation-sensitive, too.

Examples for light curable impression materials are given in EP 2 380 925 A1 (3M), U.S. Pat. No. 5,145,886 (Oxman et al.), EP 0 398 701 B1 (3M), U.S. Pat. No. 6,376,569 B1 (Oxman et al.), EP 0 269 071 B1 (Dentsply). The content of these documents is herewith incorporated by reference.

Upon application of radiation, the radiation-sensitive composition will start to cure, which typically goes along with an increase of consistency. Such a curing or pre-polymerization takes place before the composition is inserted into the sulcus of a tooth.

Besides a radiation-sensitive curing mechanism, composition (A) may contain in addition a dark-curing mechanism, e.g. based on a redox-initiator system.

Composition (A) may also be cured by using a Lewis or Broensted acid containing initiator. These initiators are typically used for initiating or starting the curing or hardening reaction of dental impression material curing via the ring-opening of aziridino moieties.

The consistency of composition (A) can also be modified by applying ultrasound.

Means for applying ultrasound are known to the technical practitioner and include ultrasound generators.

Using ultrasonic sound as an energy source can also be used for activating the curing reaction. If desired and applicable, the physical means for modifying the consistency can be combined.

Chemical means to modify the consistency of composition (A) include increasing of the amount of catalyst or adding a modifying agent to the curable composition (A).

Composition (A) comprises curable component(s) and a catalyst or initiator suitable for curing or initiating the curing or hardening of the curable component(s).

One chemical means for modifying the consistency of composition (A) includes the increase the amount of catalyst contained in composition (A).

An increase of the amount of catalyst typically leads to an accelerated curing reaction of the curable component(s) contained in composition (A).

An increase of the amount of the catalyst can be effected by different means.

One means includes the addition of further catalyst to composition (A) before composition (A) is dispensed from the device. The further catalyst can be contained as a so-called modifying agent in a separate container or device from which the catalyst is taken on demand.

If composition (A) is provided in the form of a catalyst and base paste to be mixed, an increase of the amount of catalyst can also be achieved by adjusting the mixing ratio of catalyst and base paste, i.e. by using more catalyst paste.

Another chemical means for modifying the consistency of composition (A) includes the addition of a modifying agent to composition (A). This modifying agent is different from the catalyst being already present.

The modifying agent may be a paste, have a particulate nature or be a further, i.e. different catalyst.

According to one embodiment, the modifying agent is a paste and has a different, preferably higher consistency compared to the consistency of the curable component(s) being present in composition (A). By adding the modifying agent having a higher consistency to composition (A), the consistency of composition (A) is increased.

Components which may be contained in a modifying agent in paste form include waxes, paraffin(s), oil(s) in combination with fillers and mixtures thereof.

According to another embodiment, the modifying agent has a particulate nature. In this respect, the modifying agent may act as a kind of filler. By adding filler to composition (A), the consistency of composition (A) is typically increased.

Examples of modifying agents in particulate form include quartz, titanium dioxide, reinforcing fillers like pyrogenic silica, the fillers described in the text further below and mixtures thereof.

In another embodiment, the modifying agent can be a further catalyst being able to initiate or catalyse a further curing reaction, which may lead to an initially steep increase of the consistency of Composition (A). That is, Composition (A) with consistency (a1) contains only one catalyst or initiator system, whereas Composition (A) with consistency (a2) contains two different catalyst or initiator system, the latter one being comprised in the modifying agent.

The modifying agent to be added can be contained in a separate container or device from which the modifying agent is taken on demand.

If desired and applicable, the chemical means for modifying the consistency can be combined.

In certain embodiments composition (A) fulfils at least one or more, sometimes all of the following parameters:
curable at room temperature within 15 min;
having a Shore hardness A from 20 to 90, 10 min after a curing reaction has been initiated;
having a tensile strength of at least 1.0 MPa or 1.5 MPa according to DIN 50125.

For dental retraction purposes, composition (A) should ideally be high viscous or having a high consistency and non-flowing behaviour or properties. These properties enable the practitioner to properly place the material into the sulcus of a patient.

The nature and structure of the curable components of composition (A) is not particularly limited unless the desired result cannot be achieved.

The hardenable components of composition (A) typically comprise a backbone with at least 2 curable moieties attached to the backbone.

The curable moieties can be selected from
vinyl siloxane moieties,
allyl moieties,
or aziridino moieties.

The backbone typically comprises
dimethylsiloxane moities,
polyether moieties,
or a combination of dimethylsiloxane moieties and polyether moieties.

According to one embodiment, composition (A) comprises at least one organopolysiloxane with at least 2 aliphatically unsaturated groups.

Preferred organopolysiloxanes of this general structure are represented by the following formula:

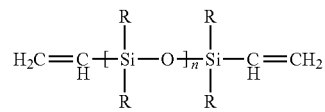

in which the radicals R, independently from each other, represent a non-substituted or substituted, monovalent hydrocarbon group with 1 to 6 C atoms, which is preferably free from aliphatic multiple bonds and where n generally can be chosen such that the viscosity of the organopolysiloxanes lies between 4 and 1,000,000 mPa*s or between 6 and 500,000 or between 10 and 100,000 mPa*s. The parameter n can, e.g., be in the range of 10 to 10,000.

The hardenable composition described in the present text may also comprise a crosslinker component capable of crosslinking the hardenable components contained in the curable composition (A).

If the hardenable components comprise vinyl moieties, the crosslinker compound is typically an organohydrogenpolysiloxane with at least 3 SiH groups per molecule.

An organohydrogenpolysiloxane typically contains from about 0.01 to about 1.7 wt.-% silicon-bonded hydrogen or from 1.0 to 9.0 mmol SiH/g. The silicon valencies which are not saturated with hydrogen or oxygen atoms are typically saturated with monovalent hydrocarbon radicals R free from ethylenically unsaturated bonds.

The hydrocarbon radicals R, which may be selected independently from each other, represent a linear or branched or cyclic, non-substituted or substituted, aliphatic or aromatic monovalent hydrocarbon groups with 1 to 12 C atoms without ethylenically unsaturated bonds. In a preferred embodiment of the invention, at least 50%, preferably 100%, of the hydrocarbon radicals R that are bonded to silicon atoms are methyl radicals.

Organohydrogenpolysiloxanes include those having a viscosity of 10 to 1,000 mPa*s or from 15 to 550 mPa*s or from 20 to 250 mPa*s.

Reactive side groups pending from or attached to the backbone may also be characterized by the following formula (I)

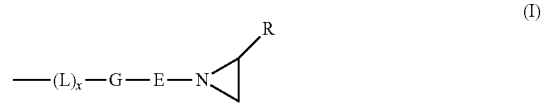

wherein
R represents H, C1-C12 alkyl, C2-C12 alkenyl, C2-C12 alkinyl, C7-C15 alkylaryl, C7-C15 arylalkyl, C3-C12 cycloalkyl, and wherein hydrogen atoms may be replaced by Cl or F and/or wherein up to five carbon atoms may be replaced by atoms or group of atoms selected from O, CO, N, S, E represents a C1-C18 branched or unbranched hydrocarbon chain wherein up to five carbon atoms may be replaced by atoms or group of atoms selected from 0, CO, N, S, G represents a group selected from C(O)O, C(O)NR, C(O), C(O)C(O), C(O)(CH2)mC(O) with m=1 to 10, C(S)NR, CH2, L represents O, S, NR with x=0 or 1.

The nature and structure of the catalyst is not particularly limited, either unless the desired result cannot be achieved.

The nature and structure of the catalyst typically depends on the nature and structure of the curable composition used.

The catalyst is able to catalyse or initiate the hardening reaction of the curable composition (A) described in the present text.

If the curable moieties of the curable component comprise vinyl moieties, the starter typically comprises a platinum containing catalyst. To effect crosslinking, a crosslinker component comprising SiH moieties is typically present or is to be added.

If the curable moieties of the curable component comprise aziridino groups, the starters are typically selected from Lewis acids, Broensted acids, pre-cursors of Lewis acids or radiation sensitive starts like iodonium salts.

Thus, useful initiators include sulfonium or iodonium salts, especially alkyl sulfonium salts or sulfonium salts derived from glutaconic acid. Those and others are described e.g. in WO 2007/016295, U.S. Pat. No. 4,167,618 and WO 2011/133495 A1 (3M). The content of these documents as regards initiators is herewith incorporated by reference.

Besides curable components and catalyst, composition (A) may contain additional components being suitable for retraction and/or impressioning purposes. Composition (A) may comprise in addition at least one or more of the following components:
filler(s),
astringent(s),
surfactant(s).

Adding filler(s) to composition (A) allow the adjustment of the consistency of composition (A).

The filler is preferably an inorganic filler and can be comprised of one type of filler or a mixture of different types of fillers.

The nature of the filler is not particularly limited. The size of the filler particles should be such that a homogeneous mixture with the hardenable component(s) forming the resin matrix of composition (A) can be obtained.

The BET surface of the filler is typically in a range from 0.05 to 50 m²/g or from 0.5 to 30 m²/g or from 0.5 to 20 m²/g. Using a filler with a BET surface within this range can be beneficial to adjust the viscosity and tensile strength.

If desired, the BET surface of the filler can be determined as described in DIN 66132.

The size of the filler particles should be such that a homogeneous mixture can be obtained. The particle distribution is preferably chosen such that there are no fillers with particle sizes of more than 200 μm.

Typically, the size of the filler particles (d50 value) is below 40 μm or below 10 μm or below 5 μm. Suitable ranges (d50 value) include from 0.1 to 40 μm or from 0.5 to 20 μm or from 1 to 10 μm.

The mean particle size, if desired, can be obtained from the cumulative curve of the grain size distribution and is defined as the arithmetic average of the measured grain sizes of a certain powder mixture. Respective measurements can be done using commercially available granulometers (e.g. CILAS Laser Diffraction Particle Size Analysis Instrument).

The term d50/μm with regard to particle size measurement means that in 50% of the analyzed volume, the particles have a size below x μm. E.g., a particle size value of below 100 μm (d50/μm) means that within the analyzed volume, 50% of the particles have a size below 100 μm.

If the filler particles are too small, the viscosity of the resulting composition might increase to a not desirable limit.

If the filler particles are too big, the detail accuracy might be negatively affected.

The filler comprises typically a filler body and a filler surface. The filler is typically in particle form.

The filler body typically comprises, consists essentially of or consists of $SiO_2$ moieties. Typical examples include quartz, cristobalite and silicates (e.g. components comprising anions of the formula $[SiO_3^{2-}]_n$ or $[Si_2O_5^{2-}]_n$) like wollastonite, nephelinsyenite, kaolin, talcum, feldspar, and mixtures thereof, wherein quartz and cristobalite are sometimes preferred.

Composition (A) may also comprise one or more surfactant(s).

Adding surfactant(s) to composition (A) may help to increase the hydrophilicity of composition (A). The better the hydrophilicity of composition (A), the better the detail reproduction of the dental tissue typically is.

Surfactants or hydrophilizing agents which can be employed can generally be chosen freely from all types of surfactants which improve the hydrophilicity of a silicone moiety containing material (especially, if curable via a hydrosilylation reaction).

Useful surfactants can generally be chosen from anionic, cationic or non-ionic surfactants or mixtures of two or more of such types of surfactants.

It can be preferred, if the hardenable composition comprises a non-ionic surfactant as a hydrophilizing agent or a mixture of two or more non-ionic surfactants. Ethoxylated fatty alcohols can be used. Suitable examples are e.g. described in EP 0 480 238 B1.

Also preferred are non-ionic surface-active substances including nonylphenolethoxylates, polyethylene glycol-mono- and diesters, sorbitan esters and polyethylene glycol-mono- and diethers. Suitable examples are described e.g. in U.S. Pat. No. 4,782,101. The content of these documents with regard to hydrophilizing agents and their preparation is herewith incorporated by reference.

Suitable hydrophilizing agents also include wetting agents from the group of hydrophilic silicone oils, which are not capable of being covalently incorporated into the hardened polymer network. Suitable hydrophilizing agents are described e.g. in U.S. Pat. No. 4,657,959 and in EP 0 231 420 B1. The content of these documents with regard to hydrophilizing agents and their preparation is herewith incorporated by reference.

Suitable silicone moieties containing surfactants can be summarized under the following formula (III)

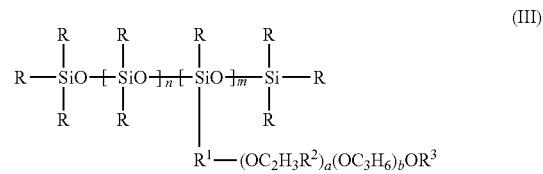

where each R is independently a monovalent hydrocarbyl radical with 1 to 22 C-atoms, $R^1$ is a divalent hydrocarbylene radical 1 to 26 C-atoms, each $R^2$ is independently hydrogen or a lower hydroxyalkyl radical, $R^3$ is hydrogen or a monovalent hydrocarbyl radical with 1 to 22 C-atoms, n and b are independently greater than or equal to zero, and m and a are independently greater than or equal to one, with the proviso that a has a sufficient value and b is small enough so that a cured composition of the invention has the desired water contact angle.

Preferably R and R³ are —CH₃, R¹ is —C₃H₆—, R² is hydrogen, n is zero or one, m is one to five, a is five to 20 and b is 0.

Several of such ethoxylated surfactants are for example available from Momentive Performance Materials Inc. including "SILWET" surface active copolymers. Preferred surface active copolymers include Silwet 35, Silwet L-77, Silwet L-7600 and Silwet L-7602, Silwet L-7608 and Silwet Hydrostable 68 and Silwet Hydrostable 611. Silwet L-77 is an especially preferred ethoxylated surfactant which is believed to correspond to the above formula where R and R³ are —CH₃, R¹ is —C₃H₆—, R² is hydrogen, n is zero or one, m is one or two, a is seven, and b is 0. Also possible is the use of MASIL® SF19, as obtainable from Lubrizol performance products, Spartanburg, US.

Useful surfactants also include polyether carbosilanes of the general formula Q-P—(OC$_n$H$_{2n}$)$_x$—OT, in which Q stands for R₃—Si— or R₃—Si—(R'—SiR₂)$_a$—R'—SiR"₂— where every R in the molecule can be the same or different and stands for an aliphatic C₁-C₁₈, a cycloaliphatic C₆-C₁₂ or an aromatic C₆-C₁₂ hydrocarbon radical, which can optionally be substituted by halogen atoms, R' is a C₁-C₁₄ alkylene group, R" is R in the case of a≠0 or is R or R₃SiR' in the case of a=0, and a=0-2; P stands for a C₂-C₁₈ alkylene group, preferably a C₂-C₁₄ alkylene group or A-R'", where A represents a C₂-C₁₈ alkylene group and R'" a functional group from the following list: —NHC(O)—, —NHC(O)—(CH2)$_{n-1}$—, —NHC(O)C(O)—, —NHC(O)(CH2)$_v$C(O)—, —OC(O)—, —OC(O)—(CH2)$_{n-1}$—, —OC(O)C(O)—, —OC(O)(CH₂)$_v$C(O)—, —OCH₂CH(OH)CH₂OC(O)(CH₂)$_{n-1}$—, OCH₂CH(OH)CH₂OC(O)(CH₂)$_v$C(O)— with v=1-12; T is H or stands for a C₁-C₄ alkyl radical or a C₁-C₄ acyl radical; x stands for a number from 1 to 200 and n stands for an average number from 1 to 6, preferably 1 to 4. Thus, the element —SiR"₂— can also comprise the substructure —Si(R)(R₃SiR')—.

Examples of useful non-ionic surfactants include those according to the formula:

R¹—O—[CH₂CH₂O]$_n$—[R²O]$_m$—R³ wherein R¹ represents an aromatic or aliphatic, linear or branched hydrocarbon group having at least 8 carbon atoms, R² represents an alkylene having 3 carbon atoms, R³ represents hydrogen or a C1-C3 alkyl group, n has a value of 0 to 40, m has a value of 0 to 40 and the sum of n+m being at least 2.

In addition to the hydrophilazing agent(s) mentioned above, the composition may also comprise an one or more F-containing component as hydrophilating agent.

Suitable examples of the F-containing compound include:

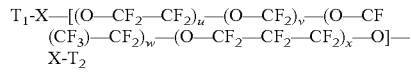

T₁-X—[(O—CF₂—CF₂)$_u$—(O—CF₂)$_v$—(O—CF(CF₃)—CF₂)$_w$—(O—CF₂—CF₂—CF₂)$_x$—O]—X-T₂ with u=0 to 8, v=0 to 8, w=0 to 14 and x=0 to 8 and u+v+w+x≥1, wherein T₁ and T₂ can be equal or different and are independently selected from the group consisting of —COOR, —CONR$^b$R$^c$—CH₂OH, —CF₂OR, —CHFOH, —CHFOR, —CH₂OR or —F with R and being a linear or branched alkyl rest (C1 to C9), aryl rest (C1 to C9) or alkylaryl rest (C1 to C9) each of which may optionally be substituted with one or more substituents selected from the group consisting of hydroxyl, amino group, halogen atom, an SiH group and a group capable of reacting with SiH, R$^b$ and R$^c$ independently representing H or having a meaning as given for R, and wherein X is selected from (CF₂)$_{1-6}$, CF(CF₃) and CHF—CF₂.

Composition (A) may also comprise one or more astringents.

Astringent(s) which may be included comprise aluminum salts like aluminum sulfate, aluminum ammonium sulfated, aluminum chlorohydrated, aluminum acetate and mixtures thereof. Useful astringent(s) can also contain iron, manganese and/or zinc containing substances.

If desired, substances like adrenaline, ephedrine, or mixtures thereof may also be added.

Incorporating an astringent into composition (A) may help to prevent or reduce the risk of bleeding during use or after removal of composition (A) from the mouth of a patient.

Thus, the composition (A) described in the present text is for use in a process for taking a dental impression and/or conducting a dental retraction, the process comprising the steps of
(a) providing a composition (A) having the consistency (a1),
composition (A) comprising curable components, and a catalyst suitable to initiate or catalyze the curing of the curable components,
composition (A) being contained in a device,
(b) applying a portion (I) of composition (A) having consistency (a2) into the sulcus of a tooth,
(c) applying a portion (II) of composition (A) having consistency (a1) in contact with composition (A) applied in step (b),
(d) removing portion (I) together with portion (II) of composition (A) from the surface of the tooth,
consistency (a2) being higher than consistency (a1),
the change in consistency of portion (I) of composition (A) to consistency (a2) being accomplished by a modifying step.

When conducting the process described in the present text and for removal of hardened composition (A) from the dental tissue, a composition (B) can be used.

Composition (B) may be characterized as follows:
curable at room temperature within 15 min;
having a Shore hardness A from 30 to 90, 10 min after the curing reaction has been initiated (e.g. by mixing a base and a catalyst paste) and/or
having a tensile strength of at least 1.0 MPa or 1.5 MPa according to DIN 50125.

The chemical nature of composition (B) is typically similar to the chemical nature of composition (A).

Chemical nature means that the curing mechanism (e.g. hydrosilation or curing by a cationic ring opening reaction) and/or the structure of the hardenable moieties of the curable components contained in the curable composition (A) and (B), respectively, are similar or identical.

If the hardenable components contained in composition (A) and composition (B) are of a similar chemical nature (e.g. bearing the same hardenable moieties), the adhesion of composition (B) to the cured composition (A) is facilitated. This allows an easier removal of the hardened compositions (A) and (B) in the final step of the dental impressioning process.

Composition (B) is typically applied with the aid of a dental impression tray, that is, composition (B) is filled in a dental impression tray and the tray is inserted into the mouth of a patient such that composition (B) is in contact with composition (A).

After curing of composition (B), composition (B) is removed from the mouth of the patient together with composition (A) being now fixed or attached to composition (B).

Composition (A) is typically provided as a kit of parts comprising a base part and a catalyst part.

The base part typically comprises the curable components and the catalyst part comprises the catalyst. The other component(s) can be present either in the base part or the catalyst part or both. Providing composition (A) as a kit of parts may be desired to increase the shelf life. The base part and the catalyst part are mixed shortly before use.

If composition (A) is provided as a kit of parts comprising a base part and a catalyst part, the consistency (a1) of composition (A) is determined based on the mixture obtained when mixing the compositions of the base part and the catalyst part.

If the modifying step is done by applying physical and/or chemical means, the consistency (a2) is determined after the application of the physical and/or chemical means. The kit may optionally comprise a modification part.

The modification part typically comprises a modifying agent as described in the present text.

The modifying agent can be selected e.g. from particulate components, pastes, additional catalyst, or a mixture or combination thereof.

A further embodiment is directed to a kit of parts comprising
   composition (A) as described in the present text;
   an instruction of use describing the process steps as described in the present text;
   optionally a composition (B) as described in the present text;
   optionally a dispenser for dispensing curable composition (A) and/or (B);
   optionally mixing means, including static or dynamic mixing tips.

Suitable dispensers for dispensing the curable composition include manually or electrically driven dispensers having a receptacle for receiving the device or container containing composition (A).

The instruction of use advices the practitioner how compositions (A) and/or (B) are to be used.

The invention is also directed to a composition (A) comprising curable components, and a catalyst suitable to initiate or catalyze the curing of the curable components, the composition being contained in a device comprising a nozzle, the composition for use in a process comprising the following steps:

(a) providing the composition (A), composition (A) having the consistency (a1), (b) modifying a portion (I) of composition (A) having consistency (a1) to be dispensed from the device to a consistency (a2), (c) applying the portion (I) of composition (A) having consistency (a2) typically through a nozzle into the sulcus of a tooth, (d) applying a portion (II) of composition (A) having consistency (a1) on top of composition (A) applied in step (c) preferably that the visible surface of the tooth is covered, (e) removing portion (I) together with portion (II) of composition (A) from the surface of the tooth, consistency (a2) being higher than consistency (a1).

In the following table different embodiments of the process described in the present text are given:

TABLE 1

| Procedural Step | Material | Curing status of Composition | Consistency | Means for Modification |
|---|---|---|---|---|
| Provision of CA | CA | CA curable | CA-a1 | |
| Modifying step | CA1 | CA1 curing | CA1-a2 | physical or chemical means |
| Application of CA1 to sulcus | CA1 | CA1 curing | CA1-a2 | |
| CA1 remains in sulcus | CA1 | CA1 curing | CA1-a2 | |
| Application of CA2 in contact with CA1 | CA1<br>CA2 | CA1 curing<br>CA2 curing | CA1-a2<br>CA2-a1 | |
| Application of tray with CB | CA1<br>CA2<br>CB | CA1 curing<br>CA2 curing<br>CB curing | CA1-a2<br>CA2-a1<br>CB | |
| Curing of CA2 being in contact with CA1 | CA1<br>CA2<br>CB | CA1 cured<br>CA2 cured<br>CB cured | CA1-a3<br>CA2-a3<br>CB-a3 | physical or chemical means |
| Removal of CA1, CA2 and CB | CA1<br>CA2<br>CB | CA1 cured<br>CA2 cured<br>CB cured | CA1-a3<br>CA2-a3<br>CB-a3 | |

CA: Composition (A); CA1: Portion (I) of composition (A); CA2: Portion (II) of composition (A); CB: Composition (B); CA-a1: composition (A) with consistency a1; CA1-a2: Portion 1 of composition (A) with consistency a2; CA1-a3: Portion 1 of composition (A) with consistency a3; CA2-a1: Portion 2 of composition (A) with consistency a1.

The consistencies are in the following order: a1 (in mm)<a2 (in mm)< or =a3 (in mm), if determined according to the method described in the Example section. A composition with consistency a3 is classified as being cured.

All components used in the dental composition of the invention should be sufficiently biocompatible, that is, the composition should not produce a toxic, injurious, or immunological response in living tissue.

The process described in the present text does typically not involve the use or application of dental retraction cords, the production or application of foams or combinations thereof.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. The above specification, examples and data provide a description of the manufacture and use of the compositions and methods of the invention. The invention is not limited to the embodiments disclosed herein. One skilled in the art will appreciate that many alternative embodiments of the invention can be made without departing from the spirit and scope of thereof.

The following examples are given to illustrate, but not limit, the scope of this invention. Unless otherwise indicated, all parts and percentages are by weight.

Examples

Unless otherwise indicated, all parts and percentages are on a weight basis, all water is de-ionized water, and all molecular weights are weight average molecular weight. Moreover, unless otherwise indicated all experiments were conducted at ambient conditions (23° C.; 1013 mbar).

Methods

Shore Hardness A

If desired, the Shore hardness was determined according to DIN 53505:2000-08.

Residual Gap Behavior/Consistency

The capability of a curable paste to open a sulcus and to keep a sulcus open during setting time of the paste can be determined by a device using a stamp which creates pressure created by a spring onto the curable paste in a small slit (residual gap device).

More precisely, the method can be described as follows:

A mold having a rectangular shape with the dimensions: x (depth)=7.5 mm, y (width)=18.0 mm and z (height)=12.0 mm is provided.

The mold (1) is formed by three immovable sidewalls (1a), (1b), (1c) and one movable sidewall (1d), all located on a plane surface (2). The movable sidewall (1d) is equipped with a spring (3) having a defined spring pressure of 20N. The spring is compressed and fixed by a removable fixation means (4). The moveable sidewall (1d) is adjusted to a pre-defined depth of 7.5 mm (x-direction). A device for determining the consistency is shown in FIG. 1. The mold is filled with the (curable) composition.

After a pre-defined time T1, the fixation means (4) of the spring (3) is removed having the result that the spring (3) exerts a predefined pressure on the (curable) composition through the movable sidewall (1d). A portion of the (curable) composition is pressed out of the mold (1). The depth of the mold is decreasing which can be determined by measuring the distance for x (mm) using e.g. a length gauge (5).

After a pre-defined time T2, the value for x (mm) is determined.

The higher the value x at time T2 is, the higher the consistency/residual gap behavior of the composition is.

For all results reported below, T1=60 s from start of applying the modification step; T2=70 s from start of applying the modification step.

If the modification step is effected by chemical means, e.g. by mixing different compositions, T1 and T2 start with the beginning of mixing the compositions.

Elongation at Break and Tensile Strength

If desired, the elongation at break and tensile strength can be determined according to DIN 53504:2009:10.

Mean Particle Size

If desired, the mean or average particle size of a powder can be obtained from the cumulative curve of the grain size distribution and is defined as the arithmetic average of the measured grain sizes of a certain powder mixture. Respective measurements can be done using commercially available granulometers (e.g. CILAS Laser Diffraction Particle Size Analysis Instrument).

Viscosity

If desired, the viscosity can be measured at 23° C. using a Haake Rotovisco 1 device with a plate/plate system (diameter 20 mm) and a slit of 0.2 mm. The viscosity values (Pas) and share stress values (Pa) can be recorded for each share rate (starting from 10 1/s to 110 1/s in 10 1/s steps. For each share rate, a delay of 5 seconds was used before collecting data. The above mentioned method of measurement corresponds essentially to DIN 53018-1.

Water Contact Angle

If desired, the water contact angle of the uncured paste can be measured as follows: Test specimen preparation: For the preparation of test piece the mixed paste is subjected to an object slide and flattened and triturated by a second object slide in order to obtain a thin film. The test piece preparation is performed in that simplified way as the thickness of the film does not have a significant effect on the measured water contact angle (see G. Kugel, T. Klettke, J. A. Goldberg, J. Benchimol, R. D. Perry, S. Sharma, J. Prosthod. 2007, 16, 84-92). Measurement: The object slide is placed on the table of a Drop Shape Analyse System DSA 10 (Krüss GmbH, Hamburg), a well known device for measuring contact angles. 5 µl of water are placed onto the surface of the specimen and an automatic contact angle measurement is started using standard software of the goniometer. Measuring time is at least about 10 s up to about 200 s. The water contact angle is measured at different time periods after mixing of base paste and catalyst paste, especially after 25 s. The data (video sequences) is evaluated by the "circle fitting" method, another standard method for data evaluation (see G. Kugel, T. Klettke, J. A. Goldberg, J. Benchimol, R. D. Perry, S. Sharma, J. Prosthod. 2007, 16, 84-92); Θ 2 s is the angle obtained 2 s after placing the water drop on the surface.

Materials

TABLE 2

| Name | Description |
|---|---|
| Imprint™ 4 Super Quick Light | Commercially available dental wash impression material; 3M ESPE Dental |
| Vinyl-terminated Polydimethylsiloxane, 2,000 mPa * s (23° C.) | Curable matrix |
| Hydrophobic fumed silica | Filler |
| Cristobalite filler | Filler |
| Platinum tetramethyldivinyldisiloxane complex 1.3 wt.-% Pt in silicone oil | Addition cure catalyst |
| Blue pigment | Additive |

General Description

Modification Agent MA1 has been prepared by homogenizing the respective components (Table 1) to a uniform paste using a planetary mixer with vacuum capabilities (Speedmixer DAC 600.1 VAC-P).

TABLE 3

Table 3 Composition of Modification Agent MA1

| Component | Weight-% |
|---|---|
| Divinylpolydimethylsiloxane 2,000 mPa * s (23° C.) | 40.00 |
| Hydrophobic fumed silica | 4.95 |
| Crystaline silica filler | 50.00 |
| Platinum tetramethyldivinyldisiloxane complex 1.3 wt.-% Pt in silicone oil | 5.00 |
| Blue pigment | 0.05 |

2.5 parts by weight of Imprint™ 4 Super Quick Light Base paste and 2.5 parts by weight of Imprint™ 4 Super Quick Light Catalyst paste has been homogenously mixed with a spatula with 1 part by weight of Modifying Agent A1. The residual gap behavior of this mixture was determined according to the description given above. In addition, the residual gap behavior of Imprint™ 4 Super Quick Light (without modification) has been determined for comparison and the results are summarized in the Table 4 below.

TABLE 4

| | Residual gap [mm] | Composition |
|---|---|---|
| Without modification | 0.05 | Imprint™ 4 Super Quick Light |
| With modification | 7.36 | Imprint™ 4 Super Quick Light + MA1 |

Results/Finding: It has been found that the consistency of Imprint™ 4 Super Quick Light can easily be modified by e.g. adding a modification agent.

The invention claimed is:

1. A process for taking a dental impression, the process comprising:
   (A) providing an unhardened composition (A) having a first consistency (a1), wherein the unhardened composition (A) comprises curable components and a catalyst suitable to initiate or catalyze curing of the curable components;
   (B) modifying the consistency of the unhardened composition (A) to have a second consistency (a2), wherein the second consistency (a2) is greater than the first consistency (a1) such that the composition (A) having the second consistency (a2) has a reduced flowing behaviour under load at the second consistency (a2) relative to the first consistency (a1) of the unhardened composition (A);
   (C) applying a first portion (I) of the composition (A) having the second consistency (a2) into a sulcus of a tooth;
   (D) applying a second portion (II), different from the first portion (I), of the composition (A) having the first consistency (a1) on top of the first portion (I) of the composition (A) applied in step (C) such that the first portion (I) of the composition (A) and the second portion (II) of the composition (A) contact and adhere to each other; and
   (E) removing the portion (I) of the composition (A) having the second consistency (a2) together with the portion (II) of the composition (A) having the first consistency (a1) from a surface of the tooth.

2. The process of claim 1, wherein the consistency of composition (A) is modified by physical means.

3. The process of claim 1, wherein the consistency of composition (A) is modified by application of heat, radiation, ultrasound or a combination thereof.

4. The process of claim 1, wherein the consistency of composition (A) is modified by chemical means.

5. The process of claim 1, wherein the consistency of composition (A) is modified by conducting either of the following steps:
   increasing the amount of catalyst;
   adding a modifying agent to the curable composition (A);
   the modifying agent being selected from particulate components, non-curable components, curable components, and mixtures, thereof.

6. The process of claim 1, comprising in addition the following steps:

applying a curable composition (B) in contact with the second portion (II) of the composition (A) applied in step (D), removing composition (B) together with the first portion (I) and the second portion (II) of the composition (A), wherein composition (B) differing from composition (A) by at least one of the following properties:

consistency before curing;

viscosity before curing;

Shore hardness A after curing;

or a combination thereof.

7. The process of claim 1, wherein the first consistency (a1) of Composition (A) is less than or equal to one half the second consistency (a2) of Composition (A).

8. The process of claim 1, wherein a volume of the first portion (I) of the composition (A) is less than or equal to one half the volume of the second portion (II) of the composition (A).

9. The process of claim 1, wherein composition (A) comprises a base part and a catalyst part, the base part comprising the curable components and the catalyst part comprising the catalyst.

10. The process of claim 1, wherein composition (A) is characterized by at least one or more of the following features:

curable at room temperature within 10 min;

having a Shore hardness A from 20 to 90, 10 min after curing has been initiated; and having a tensile strength of at least 1 MPa according to DIN 50125.

11. The process of claim 1, wherein the composition (A) further comprises at least one or more of the following components:

filler(s);

astringent(s);

surfactant(s); and combinations thereof.

12. The process of claim 1, wherein the curable components of composition (A) comprise a backbone with at least 2 curable moieties attached to the backbone; the curable moieties being chosen from: vinyl siloxane moieties; or aziridino moieties; and the backbone comprising dimethylsiloxane moities; polyether moieties; or a combination of dimethylsiloxane moieties and polyether moieties.

* * * * *